United States Patent [19]

Horrobin et al.

[11] Patent Number: 5,145,686
[45] Date of Patent: Sep. 8, 1992

[54] TOPICAL PHARMACEUTICAL COMPOSITIONS

[75] Inventors: David F. Horrobin, Montreal, Canada; Julian Lieb, Bethany, Conn.

[73] Assignee: Efamol Limited, London, United Kingdom

[21] Appl. No.: 818,501

[22] Filed: Jan. 8, 1992

Related U.S. Application Data

[63] Continuation of Ser. No. 312,730, Feb. 17, 1989, abandoned, which is a continuation of Ser. No. 89,035, Aug. 24, 1987, abandoned, which is a continuation of Ser. No. 786,517, Oct. 11, 1985, abandoned, which is a continuation of Ser. No. 458,466, Jan. 17, 1983, abandoned, which is a continuation-in-part of Ser. No. 345,204, Feb. 3, 1982, abandoned.

[51] Int. Cl.[5] .................... A61K 33/14; A61K 33/04; A61K 33/00; A61K 31/61
[52] U.S. Cl. .................... 424/677; 424/709; 424/715; 514/163; 514/552; 514/574
[58] Field of Search ............... 424/677, 722, 709, 715; 514/574, 163, 552

[56] References Cited

U.S. PATENT DOCUMENTS

| | | | |
|---|---|---|---|
| 3,527,864 | 9/1970 | MacMillan et al. | 424/59 |
| 3,639,625 | 2/1972 | Sherwin | 424/153 |
| 4,302,447 | 11/1981 | Horrobin | 424/145 |
| 4,386,072 | 5/1983 | Horrobin et al. | 424/127 |

OTHER PUBLICATIONS

*Remington's Pharm. Sciences*, pp. 353 & 733 (1980).
Ando et al., *Chem. Abst.* 88:65874z (11/8/77).
Queuauviller et al., *Chem. Abst.* 88:146313t (1977).
Dianzani et al., *Chem. Abst.* 91:68529p.
Mucsi et al. *Chem. Abst.* 90:67141y (1978) and 89:71525y (1977).
*FDA Consumer*, "Vitamin E-Miracles on Myth", (Aug, 1973).
*The Merck Index*, 9th ed., pp. 31 & 649 (1976).
Horrobin et al., *Chem. Abst.* 99:146126m (1983).
Passarella et al., *Chem. Abst.* 92:28475g (1980).
Punnoneu et al., *Chem. Abst.* 107:3394v (1987).

*Primary Examiner*—Frederick E. Waddell
*Assistant Examiner*—Raymond J. Henley, III
*Attorney, Agent, or Firm*—Foley & Lardner

[57] ABSTRACT

Topical pharmaceutical compositions for the treatment of lesions of the skin or mucous membranes containing a physiologically acceptable lithium salt together with at least one substance selected from substances capable of selectively increasing the in vivo level of E-series prostaglandins, substances capable of inhibiting cyclooxygenase enzyme, substances capable of inhibiting the formation of lipoxygenase products, and lysine.

4 Claims, No Drawings

TOPICAL PHARMACEUTICAL COMPOSITIONS

This application is a continuation of application Ser. No. 07/312,730, filed Feb. 17, 1989 now abandoned, which is a continuation of U.S. application Ser. No. 07/089,035 (filed Aug. 24, 1987), now abandoned, which is a continuation of U.S. application Ser. No. 06/786,517 (filed Oct. 11, 1985), now abandoned, which was a continuation of U.S. application Ser. No. 06/458,466 (filed Jan. 17, 1983), now abandoned, which was a continuation-in-part of U.S. application Ser. No. 06/345,204 (filed Feb. 3, 1982), now abandoned.

BACKGROUND OF THE INVENTION

This invention relates to topical pharmaceutical compositions and their use in the treatment of lesions of the skin and mucous membranes.

The oral and parenteral administration of lithium and in particular lithium salts such as lithium carbonate, has found widespread application in the treatment of manic-depressive psychosis. Lithium treatment has been reported as being particularly effective in the treatment of the manic phase of this illness and also in the prophylaxis of both manic and depressive relapses.

It has been reported (Lieb, N.Eng.J.Med. 301(1979), 942) that the oral administration of lithium salts in the treatment of manic-depressive illness has been accompanied by the remission of recurrent herpes infection in a patient additionally suffering from labial herpes and in a patient also having genital herpes.

U.S. Pat. No. 3,639,625 (issued Feb. 1972 to Sherwin) describes therapeutic compositions containing lithium succinate for treating dermatitis and for producing an antipruritic effect, the compositions thus being suitable for topical application.

Our copending Application Ser. No. 251901 filed Apr. 7, 1981, now U.S. Pat. No. 4,328,243, describes a method for the treatment of the side-effects of lithium treatment in a subject suffering from manic-depressive psychosis and undergoing lithium treatment by orally administering to the subject an effective amount of dihomo-$\gamma$-linolenic acid and/or $\gamma$-linolenic acid or linoleic acid.

SUMMARY OF THE INVENTION

We now propose that the conjoint topical administration of lithium with one or more substances selected from substances capable of selectively increasing the in vivo level of E-series prostaglandins, substances capable of inhibiting cyclooxygenase enzyme, substances capable of inhibiting the in vivo formation of lipoxygenase products, and lysine will be effective in the treatment of lesions of the skin and mucous membranes.

Thus, in one aspect, the invention provides a pharmaceutical composition for topical administration which comprises at least one physiologically acceptable lithium salt together with at least one substance selected from substances capable of selectively increasing the in vivo level of E-series prostaglandins, substances capable of inhibiting cyclooxygenase enzyme, substances capable of inhibiting the formation of lipoxygenase products, and lysine.

DETAILED DESCRIPTION OF PREFERRED EMBODIMENTS

Lesions of the skin and of mucous membranes are generally associated with an inflammatory response, and, in turn, inflammation is believed to be due in part to excessive and/or defective production of certain prostaglandins and related substances. Prostaglandins and related substances are biosynthesised in the body from two main substances, dihomo-$\gamma$-linolenic acid and arachidonic acid. In general, prostaglandins of the E-series exhibit a beneficial anti-inflammatory activity, and while minor amounts of such prostaglandins are formed from arachidonic acid, most of the prostaglandin products derived from arachidonic acid show an inflammatory action. The principal prostaglandin product derived from dihomo-$\gamma$-linolenic acid is prostaglandin E1 which exhibits the anti-inflammatory activity. Concomitant with the production of prostaglandins and related substances from dihomo-$\gamma$-linolenic acid and arachidonic acid by the cyclooxygenase enzyme, other bioproducts are formed from these acids as a result of the action of the enzyme, lipoxygenase. These lipoxygenase products also exhibit an inflammatory action.

Dihomo-$\gamma$-linolenic acid and arachidonic acid for metabolism in the body to prostaglandins and lipoxygenase products are usually available either from endogenous stores of these acids or from food sources. For example, dihomo-$\gamma$-linolenic acid may be biosynthesized from dietary sources of its precursor substances $\gamma$-linolenic acid and linoleic acid. In animals arachidonic acid may readily be biosynthesised from dihomo-$\gamma$-linolenic acid, but in adult humans such a mechanism is not particularly effective so that the major source of arachidonic acid for prostaglandin synthesis may be from ingestion of the acid per se.

We now believe that the previously noted activity of lithium succinate for treating dermatitis and for producing an antipuritic effect is due to the ability of lithium to block the release of dihomo-$\gamma$-linolenic acid and arachidonic acid from endogenous stores of these compounds, so that the availability of the compounds for conversion to the inflammatory prostaglandins and lipoxygenase products is reduced.

However, as indicated above, E-series prostaglandins are believed to be benefical in the treatment of skin and mucous membrane lesions due to their anti-inflammatory activity, so that in one embodiment, the compositions according to the invention incorporate one or more substances which are capable of selectively increasing the in vivo level of E-series prostaglandins.

For example, the in vivo level of E-series prostaglandins and especially prostaglandin $E_1$ may be increased by incorporating dihomo-$\gamma$-linolenic acid and/or its bioprecursors such as $\gamma$-linolenic acid and linoleic acid into the compositions, conveniently in an amount of from 0.01 to 80, preferably from 1 to 15, percent by weight. If desired, the level of E-series prostaglandins may be increased by including a substance which acts to mobilise the endogenous stores of dihomo-$\gamma$-linolenic acid and examples of such substances include physiologically acceptable zinc salts, conveniently in an amount sufficient to provide from 0.01 to 10, preferably 0.1 to 5 percent by weight of zinc ions. This object may also be achieved by including in the composition a substances which is capable of activating the bioconversion of dihomo-$\gamma$-linolenic acid to E-series prostaglandins such as, for example, ascorbic acid (e.g. in an amount of from 0.01 to 20, preferably 0.1 to 5 percent by weight), ethanol (e.g. in an amount of form 0.01 to 80, preferably 0.1 to 10% percent, by weight) and spironolactone, (e.g. in an amount of from 0.01 to 20, preferably 0.1 to 5, percent by weight).

In the body, E-series prostaglandins may themselves act as bioprecursors for other prostaglandins. For example, prostaglandin $E_1$ may be converted to prostaglandin $F_1\alpha$, which does not show the desired anti-inflammatory action. The level of E-series prostaglandins may therefore be increased by incorporating a substance which is capable of blocking their bioconversion to other prostaglandins. Examples of such substances are rutin and other bioflavanoids. Rutin may conveniently be incorporated into the compositions in an amount of from 0.01 to 20, preferably 0.1 to 10 percent by weight.

As indicated above, prostaglandins of the E-series form only a minor proporation of the prostaglandin products of the metabolism of arachidonic acid. As the major proportion of the prostaglandin products from arachidonic acid do not provide an anti-inflammatory action, it may therefor be desirable to incorporate into the compositions of the invention a substance which is capable of selectively promoting the formation of E-series prostaglandins in the bioconversion of arachidonic acid. An example of a substance which may be used for this purpose is glutathione, conveniently in an amount of 0.01 to 20, preferably 0.1 to 5, percent by weight of the composition. It may also be desired to include in the composition a substance which is capable of blocking the conversion of arachidonic acid to any prostaglandin. One such substance which may be used is (20:5n3) eicosapentaenoic acid and this may conveniently be present in an amount of from 0.01 to 20, preferably 0.1 to 5, percent by weight.

As indicated the biosynthesis of prostaglandins from dihomo-γ-linolenic acid and arachidonic acid by the cyclo-oxygenase enzyme is also associated with the formation of lipoxygenase products which themselves exhibit inflammatory activity. Thus it has been found that the biosynthesis of the prostaglandins may be inhibited or blocked by substances which are able to inhibit the cyclo-oxygenase enzyme. It has also been found that the formation of lipoxygenase products may be inhibited or blocked e.g. in the presence of vitamin E and related tocopherols. Thus, in one embodiment, the compositions according to the invention may contain one or more substances which are capable of inhibiting the cyclo-oxygenase enzyme and/or one or more substances which are capable of inhibiting the formation of lipoxygenase products optionally in addition to one or more substances which are capable of selectively increasing the in vivo level of E-series prostaglandins. Substances which are capable of inhibiting the cyclo-oxygenase enzyme include, for example, acetylsalicylic acid, indomethacin, mefenamic acid, ketoprofen, ibuprofen and paracetamol. The formation of lipoxygenase products may be inhibited by, for example, vitamin E and/or related tocopherols, or any other physiologically acceptable lipoxygenase inhibitor.

Lysine may conveniently be present in the compositions in an amount of from 0.01 to 20, preferably 0.1 to 5, percent by weight.

If edema is present, this may limit the access of therapeutic agents to cells which are inflamed or infected. It may therefore be advantageous to administer the composition of the invention in a form which is capable of reducing local edema and which will aid the penetration of the other components of the composition to the affected cells. This may be achieved by additionally incorporating one or more high molecular weight polysaccharides into the compositions. Examples of such polysaccharides include dextrans, such as dextran sulphate.

The compositions according to the invention are in a form suitable for topical administration. Examples of such forms include creams, ointments, solutions, suspensions, emulsions, lotions, gels and sprays. Such forms may be prepared with pharmaceutical carriers and excipients conventionally used for such purposes. The compositions of the invention are preferably in the form of ointments, which may conveniently be formulted using an appropriate base such as, for example, lanolin, paraffin or cetyl alcohol.

The compositions according to the invention may be used for the treatment of disorders of the skin and mucous membranes e.g. oral, nasal, ocular, aural, genital or gastrointestinal membranes. In particular, the compositions may be used in the treatment of pruritis, lesions arising from inflammatory disorders such as eczema and psoriasis and the lesions due to allergic reactions such as to poison ivy as well as having a soothing and analgesic effect on such lesions. of lesions arising from superficial wounds, burns, and local poisoning, e.g., as a result of insect bites and stings.

Thus, in a further aspect, the invention provides a method for the treatment of lesions of the skin or mucous membranes of a subject, which method comprises topically administering to said lesions an effective amount therefor of a composition according to the invention.

The lithium salts employed according to the invention will be physiologically acceptable, and examples of such salts include lithium carbonate, chloride, sulphate, citrate, succinate, salicylate and acetylsalicylate.

When the compositions according to the invention contain dihomo-γ-linolenic acid this may, if desired, be replaced, at least in part, by an equivalent amount of a biosynthetic precursor thereof such as the abovementioned γ-linolenic acid or linoleic acid. If desired, these substances may be used in admixture. These substances may also be used in the form of physiologically acceptable functional derivatives thereof such as, for example, their $C_1$-$C_4$ alkyl (e.g. methyl and ethyl) esters and the triglycerides of the acids. Convenient sources of linoleic acid for use according to the invention are the many vegetable oils of which it forms a major constituent. Examples of such oils include cotton-seed, soyabean, peanut, corn, sunflower seed, safflower, poppy seed, linseed and perilla oils, where the linoleic acid occurs in the form of its triglyceride, and the vegetable oils may be used as such i.e. without any treatment to isolate the linoleic acid therefrom.

At the present time known sources of oils having a high γ-linolenic acid content are few. One source currently available is the seed of the Evening Primrose or *Oenothera biennis* L, the oil extract therefrom containing γ-linolenic acid and linoleic acid in the form of their triglycerides. Another source of γ-linolenic acid is the seed of *Borago officinalis* which provides a richer source of γ-linolenic acid with smaller amounts of linoleic acid. Again, these seed oil extracts may be used as such or may, if desired, be fractionated to yield an oil composition enriched in the desired γ-linolenic and/or linoleic acids.

Dihomo-γ-linolenic acid for use according to the invention may be prepared from γ-linolenic acid according to known methods.

If convenient, it may be appropriate to utilise the lithium in the form of a salt with the above mentioned acids, that is with dihomo-γ-linolenic, γ-linolenic or linoleic acid.

The bioconversion of linoleic acid to γ-linolenic acid, which is itself subsequently converted to dihomo-γ-linolenic acid, is promoted in the presence of zinc. We have found that the conversion of dihomo-γ-linolenic acid to prostaglandin E1 is also enhanced by zinc. Thus, as indicated above, the compositions according to the invention may if desired contain a physiologically acceptable zinc salt such as, for example, zinc sulphate or gluconate. The use of a zinc salt in compositions of the invention may be beneficial independent of its effects on fatty acid and prostaglandin metabolism, as it may have healing properties of its own.

Compositions according to the invention conveniently contain an amount of lithium salt sufficient to provide from 0.01 to 25, preferably 1 to 5, percent by weight of lithium ions in the compositions. When the composition contains vitamin E and/or related tocopherols, these are conveniently present in an amount of 0.01 to 25, preferably 1 to 10, percent by weight.

Under certain circumstances, it may be desirable to limit the formation of all cyclo-oxygenase and lipoxygenase products from both dihomo-γ-linolenic acid and arachidonic acid. In this situation it may be appropriate to use a combination of a lithium salt and a tocopherol which is capable of inhibiting the formation of lipoxygenase products without conjointly adminstering dihomo-γ-linolenic acid or its precursors. The following Examples serve to illustrate the invention:

EXAMPLE 1

Ointment

|  | % by weight |
|---|---|
| Lithium citrate | 8 |
| Vitamin E | 1 |
| Oil of Evening Primrose | 8 |
| Zinc sulphate | 2 |
| Dextran sulphate | 2 |

The above components are formulated with an appropriate ointment base, such as a base containing one or more cetyl alcohols with non-irritant emulsifiers or a lanolin base.

EXAMPLES 2-8

Ointments

The following components are formulated in the amounts shown in Table I with an appropriate ointment base, such as those described in Example 1:

TABLE I

|  | Ex 2 | Ex 3 | Ex 4 | Ex 5 | Ex 6 | Ex 7 | Ex 8 |
|---|---|---|---|---|---|---|---|
|  | % by weight | | | | | | |
| Lithium succinate | 6 | 8 | — | — | — | 8 | 8 |
| Lithium citrate | — | — | — | 8 | 8 | — | — |
| Lithium acetyl salicylate | — | — | 5 | — | — | — | — |
| Vitamin E | 1 | 1 | 1 | 1 | 1 | 1 | 1 |
| Oil of Evening Primrose | 4 | — | — | 8 | 5 | 5 | — |
| Zinc sulphate | 2 | — | — | 2 | — | — | 2 |
| Dextran sulphate | 2 | 2 | 3 | — | — | — | 2 |

EXAMPLES 9-11

Ointments

The following components are formulated in the percent by weight amounts shown in Table II with an appropriate ointment base, such as those described in Example 1:

TABLE II

|  | Ex. 9 | Ex. 10 | Ex. 11 |
|---|---|---|---|
| Lithium succinate | 8 | — | — |
| Lithium citrate | — | 6 | 5 |
| Vitamin E | — | 1 | 2 |
| Indomethacin | 1 | — | 2 |
| Mefenamic acid | — | 2 | — |

EXAMPLES 12-25

Ointments

The following components are formulated in the percent by weight amounts shown in Table III with an appropriate ointment base, such as those described in Example 1:

TABLE III

|  | Ex. 12 | Ex. 13 | Ex. 14 | Ex. 15 | Ex. 16 | Ex. 17 | Ex. 18 | EX. 19 | Ex. 20 | Ex. 21 | Ex. 22 | Ex. 23 | Ex. 24 | Ex. 25 |
|---|---|---|---|---|---|---|---|---|---|---|---|---|---|---|
| Lithium succinate | 8 | 4 | — | — | 5 | — | — | — | 8.0 | — | — | 6.0 | — | 7.0 |
| Lithium citrate | — | — | 6 | 8 | — | 6 | — | — | — | 4.0 | — | — | 5.0 | — |
| Lithium acetyl-salicylate | — | — | — | — | — | — | 5.0 | 10.0 | — | — | 4.0 | — | — | — |
| Indomethacin | — | 0.5 | 1.0 | — | — | — | — | — | 1.0 | — | — | — | — | — |
| Vitamin E | 1.0 | 0.5 | 0.5 | 1.0 | 0.5 | 1.0 | 1.0 | 1.0 | — | — | — | — | — | — |
| Evening primrose oil | 2.0 | 1.0 | — | 2.0 | — | — | 3.0 | — | — | 2.0 | — | — | — | — |
| Dihomo-γ-linolenic acid | — | — | 2.0 | — | — | 3.0 | — | — | — | — | — | — | — | — |
| Zinc sulphate | 0.05 | 0.1 | 0.2 | — | 0.05 | — | — | 0.5 | — | — | — | — | — | — |
| Dextran sulphate | 2.0 | 2.0 | 3.0 | — | — | 1.0 | — | — | — | — | — | — | — | — |
| Spironolactone | 1.0 | 1.0 | 0.5 | — | 0.5 | — | — | — | — | — | — | 1.0 | — | — |
| Ascorbic Acid | 1.0 | 1.0 | 2.0 | — | — | 2.0 | — | 1.0 | — | — | — | — | — | — |
| Ethanol | 5.0 | 5.0 | 4.0 | — | 3.0 | — | 5.0 | — | — | — | — | — | — | — |
| Eicosapentaenoic acid | 1.0 | 1.0 | 1.0 | — | — | 5.0 | — | — | — | — | 2.0 | — | — | — |
| Glutathione | 1.0 | 1.0 | 0.5 | — | 1.0 | 0.5 | 1.0 | 2.0 | — | — | — | — | — | 2.0 |
| Rutin | 0.5 | 1.0 | 0.5 | — | — | — | 0.5 | — | — | — | — | — | — | — |

TABLE III-continued

|  | Ex. 12 | Ex. 13 | Ex. 14 | Ex. 15 | Ex. 16 | Ex. 17 | Ex. 18 | Ex. 19 | Ex. 20 | Ex. 21 | Ex. 22 | Ex. 23 | Ex. 24 | Ex. 25 |
|---|---|---|---|---|---|---|---|---|---|---|---|---|---|---|
| Lysine | 0.5 | 1.0 | 2.0 | — | — | 2.0 | 1.0 | 0.5 | — | — | — | — | 1.0 | — |

We claim:

1. A pharmaceutical composition for topical application which comprises (a) at least one physiologically acceptable lithium salt in an amount sufficient to provide about 8% by weight of lithium ions in said composition, and (b) about 3% by weight of evening primrose oil.

2. A composition as claimed in claim 1, consisting essentially of the recited ingredients.

3. A method for the treatment of lesions of the skin or mucous membranes of a subject in need of said treatment, comprising the step of topically applying to a lesion associated with an inflammatory response an antiinflammation-effective amount of a pharmaceutical composition that comprises (a) at least one physiologically acceptable lithium salt in an amount sufficient to provide about 8% by weight of lithium ions and (b) about 3% by weight of evening primrose oil.

4. A method as claimed in claim 3, wherein said pharmaceutical composition consists essentially of the recited ingredients.

* * * * *